(12) United States Patent
Sahlberg et al.

(10) Patent No.: US 7,071,830 B2
(45) Date of Patent: Jul. 4, 2006

(54) MOISTURE SENSOR

(75) Inventors: Bengt Sahlberg, Lund (SE); Johan Sjöholm, Lund (SE); Ernst Wehtje, Malmö (SE); Per-Olof Erlandsson, Södra Sandby (SE)

(73) Assignee: Bioett AB, Lund (SE)

( * ) Notice: Subject to any disclaimer, the term of this patent is extended or adjusted under 35 U.S.C. 154(b) by 0 days.

(21) Appl. No.: 10/481,827

(22) PCT Filed: Jul. 3, 2002

(86) PCT No.: PCT/SE02/01316

§ 371 (c)(1),
(2), (4) Date: Feb. 23, 2004

(87) PCT Pub. No.: WO03/012419

PCT Pub. Date: Feb. 13, 2003

(65) Prior Publication Data
US 2004/0178807 A1    Sep. 16, 2004

(30) Foreign Application Priority Data
Jul. 6, 2001   (SE) .................................... 0102426

(51) Int. Cl.
*G08B 23/00* (2006.01)
(52) U.S. Cl. ................. 340/573.5; 340/604; 200/61.04; 200/182; 604/361
(58) Field of Classification Search ............. 340/573.1, 340/573.5, 604; 200/182, 61.04, 61.05, 61.06
See application file for complete search history.

(56) References Cited

U.S. PATENT DOCUMENTS

| | | | |
|---|---|---|---|
| 3,915,804 A | 10/1975 | Messing | |
| 4,327,731 A * | 5/1982 | Powell | ........................ 604/361 |
| 4,928,513 A | 5/1990 | Sugihara et al. | |
| 5,036,859 A * | 8/1991 | Brown | ........................ 600/547 |

(Continued)

FOREIGN PATENT DOCUMENTS

EP    0 111 733 A2    6/1984

(Continued)

OTHER PUBLICATIONS

PCT International Search Report dated Sep. 26, 2003 (including 11 items cited).

*Primary Examiner*—Jeffery Hofsass
*Assistant Examiner*—George Bugg
(74) *Attorney, Agent, or Firm*—Buchanan Ingersoll PC

(57) ABSTRACT

A sensor for indicating moisture, comprising a unit whose conductivity is dependent on the current moisture exposure and an electric circuit, the unit being included as a component in the electric circuit and the electric circuit being activable by applying an electric field and/or a magnetic field over the same to generate a measurable signal, which is dependent on the total resistance of the circuit. The unit comprises an enzyme together with a substrate, which enzyme is activated when moisture exposure occurs to catalyse a reaction with the substrate that is dependent on the degree of moisture exposure, the substrate reaction product increasing the conductivity of the unit. The invention also relates to the use of such a sensor and a method of using a sensor to indicate moisture.

16 Claims, 1 Drawing Sheet

U.S. PATENT DOCUMENTS

| | | | |
|---|---|---|---|
| 5,463,377 A | 10/1995 | Kronberg | |
| 5,537,095 A * | 7/1996 | Dick et al. | 340/573.5 |
| 6,093,869 A * | 7/2000 | Roe et al. | 604/361 |
| 6,097,297 A | 8/2000 | Fard | |
| 6,384,296 B1 * | 5/2002 | Roe et al. | 604/361 |
| 6,642,016 B1 * | 11/2003 | Sjoholm et al. | 435/15 |
| 6,774,800 B1 * | 8/2004 | Friedman et al. | 340/573.5 |

FOREIGN PATENT DOCUMENTS

| | | |
|---|---|---|
| GB | 2 181 286 A | 4/1987 |
| GB | 2 183 344 A | 6/1987 |
| JP | 10030998 A | 4/1998 |
| JP | 2000093448 A | 4/2000 |
| WO | 91/03735 | 3/1991 |
| WO | 92/21959 | 12/1992 |
| WO | 99/56690 | 11/1999 |
| WO | WO 00/16081 | 3/2000 |
| WO | WO 01/25472 | 4/2001 |
| WO | WO0125472 A1 * | 4/2001 |

* cited by examiner

MOISTURE SENSOR

FIELD OF THE INVENTION

The present invention relates to a sensor. More specifically, the invention relates to a sensor for indicating moisture according to the preamble to claim 1.

BACKGROUND ART

Moisture detection is important in a number of different situations. Moisture is undesirable whether it appears in houses, textiles, packaging materials, electronic appliances, chemicals, dry foodstuffs, etc. Our industrialized society produces increasingly refined products, many of which are highly sensitive to moisture.

A plurality of prior art devices for detecting moisture are available on the market. WO0016081 discloses an electronic sensor comprising a resonant circuit. The resonant circuit comprises, inter alia, electrically conductive particles and a material that is capable of swelling in the presence of moisture. When the material swells the conductive particles are drawn apart and the conductivity of the moisture sensitive material decreases and the electrical resistance of the material increases. The electronic sensor is read by means of a detector, which generates an electromagnetic field.

U.S. Pat. No. 5,463,377 discloses a sensor comprising a circuit with two electrodes connected to a switch. The switch closes in the presence of an electrically conductive liquid between the electrodes. The switch may also close by a change in conductivity of a material between the electrodes or by expansion of a liquid absorber that pushes the electrodes together.

U.S. Pat. No. 6,097,297 discloses a sensor that is in permanent contact with the detector. The sensor comprises two conductive electrode strips which have an absorbing material located between them. When a liquid, preferably urine, is absorbed, the resistance between the electrodes changes, which sends a signal to the detector.

GB 2,183,344 discloses, inter alia, a sensor for detecting moisture. The sensor comprises a ceramic substrate with a tin oxide film, the substrate being connected on both sides to platinum electrodes. In the presence of moisture, the electrical conductivity across the substrate changes, which is detected by means of the electrodes.

U.S. Pat. No. 4,327,731 discloses a system for indicating moisture in a diaper comprising an enzyme and a substrate as well as a chromogen. In the presence of moisture, the substrate is dissolved, which catalyses reactions with the enzyme and the chromogen resulting in a coloured pigment being produced.

WO 9956690 concerns an incontinence pad based on the above-mentioned technique disclosed in U.S. Pat. No. 4,327,731. The pad is divided into zones which have varying urine absorption capacity and which undergo colour changes when exposed to moisture, thereby permitting a quantitative estimate of urine incontinence to be indicated.

In addition, there are sensors comprising an enzyme and a substrate that are adapted for other fields of use, such as the sensor disclosed in WO 0125472, which is an activable time-temperature indicator for determining and/or controlling the durability status of a product. The enzyme in this sensor is activated at a time 0 by being brought into contact with the substrate, for example in connection with the packaging of the finished product.

SUMMARY OF THE INVENTION

One object of the present invention is to provide an improved sensor, which, preferably, can be used to indicate the quantity of moisture to which the sensor is exposed.

A second object of the present invention is to provide a sensor that is capable of indicating the current moisture status in an area or a product.

A third object is to provide a moisture sensor that allows rapid, rational and objective reading.

A fourth object of the present invention is to provide a way of using a sensor for indicating moisture.

A fifth object of the present invention is to provide a method of indicating moisture by means of a sensor.

To achieve the first three objects, a sensor is provided in accordance with claim 1. Preferred embodiments are stated in claims 2–12.

To achieve the additional objects, a way of using a sensor according to claims 13, 14 and 15 and a method of measuring moisture by means of a sensor according to claim 16 are provided.

More specifically, according to the present invention a sensor for indicating moisture is defined, comprising a unit whose conductivity is dependent on the current moisture exposure, and an electric circuit, said unit being included as a component in said electric circuit and said electric circuit being activable by applying an electric field and/or a magnetic field over the same to generate a measurable signal, which is dependent on the total resistance of the circuit. The unit comprises an enzyme together with a substrate, which enzyme is activated by moisture exposure to catalyse a reaction with the substrate that is dependent on the degree of moisture exposure, the substrate reaction product increasing the conductivity of the unit.

The catalytic activity of the enzyme is dependent on the surrounding moisture. The enzyme activity results in the substrate being transformed into reaction products. Owing to the enzyme activity the quantity of reaction products increases as does also the conductivity of the unit as a function of the time and temperature at which moisture exposure occurs. The conductivity of the reaction products affects the total resistance of the circuit. When activating the electric circuit, a signal is generated that is dependent on the total resistance of the circuit, which in turn is dependent on the conductivity of the reaction products. The signal thus also indicates, besides the conductivity of the reaction products, the quantity of moisture to which the sensor has been exposed. The electric circuit is activated by applying an electric field and/or a magnetic field over the same. The signal that is generated when activating the circuit is preferably a measurable current induced in the circuit.

A preferred embodiment of the present invention will be described below for the purpose of exemplification with reference to the accompanying drawings.

DESCRIPTION OF EMBODIMENTS

Figure 1:
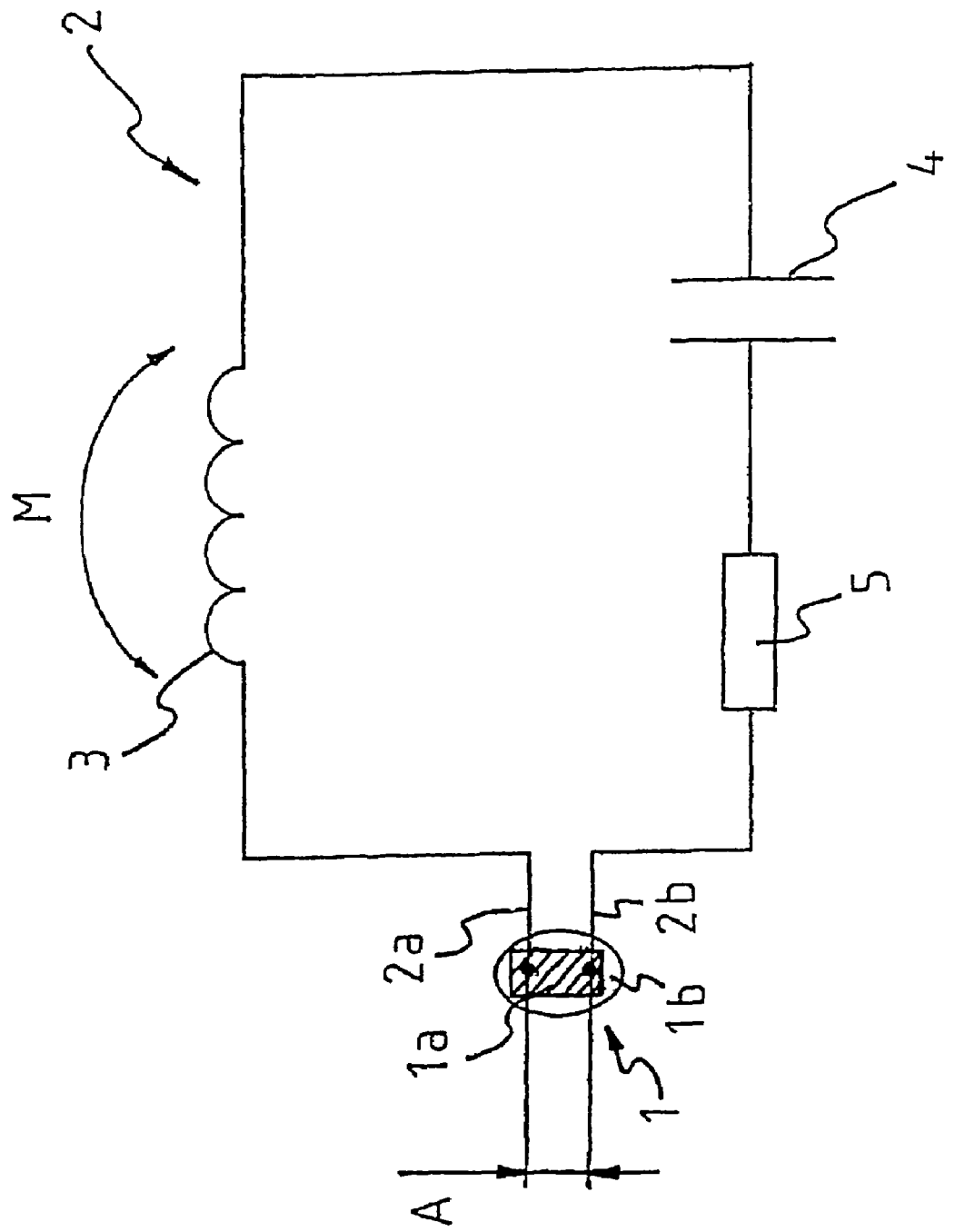
FIG. 1 is a schematic view of a sensor according to a preferred embodiment of the present invention.

Reference is now made to FIG. 1, which schematically shows a sensor according to a preferred embodiment of the present invention.

The sensor comprises a unit 1, including an enzyme 1*a* and a substrate 1*b* as well as an electric circuit 2, which is affected by said unit 1 and adapted to generate a signal when activated.

The unit 1 is preferably made of an absorbent material with good absorbing capacity, such as filter paper. The absorbent material is preferably arranged with a layer of a barrier material which allows moisture transport in one direction, i.e. which allows moisture transport from the surroundings but prevents evaporation from the absorbent material.

The enzymes 1a that are relevant to the present invention are the ones that cause a change in the conductivity of the substrate. Enzymes which catalyse a reaction, in which as many ions as possible form, are particularly preferred. The reason for this is that the relative change in conductivity is thus maximised. Enzymes having this property can be found in the following enzyme classes: Transferases, Hydrolases and Lyases.

A particularly preferred enzyme 1a is Urease, from the enzyme class Hydrolases, which by means of water catalyses a hydrolyse of Urea to form carbon dioxide and ammonia.

Both the enzyme 1a and its substrate 1b according to the present invention are thus well-defined and preferably immobilized on the absorbent material.

In one embodiment, the enzyme and the substrate are arranged in layers on the absorbent material.

When exposed to moisture, the enzyme 1a in the unit 1 is activated catalysing a reaction with the substrate 1b, whose reaction product will increase the conductivity of the unit 1 from its initial zero value when the unit was dry. The higher the moisture content in the unit 1 the higher the enzyme activity, which results in an increasing proportion of reaction products and thus higher conductivity of the unit 1. Owing to the enzyme activity the quantity of reaction products increases as does the conductivity of the unit as a function of the time and temperature at which moisture exposure occurs. In applications where the temperature is essentially constant, it is therefore possible to quantify the amount of moisture to which the sensor has been exposed.

The substrate 1b may also comprise a buffer solution in order to counteract any changes in pH of the substrate 1b. Extreme pH values capable of deactivating the enzyme 1a are thus avoided.

The unit 1 is included as a component in an electric circuit 2. The electric circuit 2, except said unit 1, is preferably insulated against the surroundings, for example by means of a plastic material, to prevent moisture from affecting the circuit, which would lead to short-circuiting thereof.

Preferably, the circuit 2 is an oscillation circuit and comprises a coil 3, a capacitor 4 and a resistor 5, which are connected in series in a closed circuit. The unit 1 is connected in series with the other components 3, 4 and 5. To activate the circuit 2, a magnetic field M is applied over the coil 3 to induce a current in the circuit 2.

As shown in FIG. 1, the unit 1 is connected to the electric circuit 2 via two electrodes 2a, 2b. In order to close the circuit 2, the substrate 1b must thus exhibit such electric conductibility that a current can flow between the electrodes 2a, 2b, the current intensity being stronger the higher the conductivity. To adapt the sensor, the distance between the electrodes 2a, 2b can be modified. Moreover, it is possible to modify the cross-sectional area of the unit 1 as well as the concentration of both the enzyme 1a and the substrate 1b. Finally, various buffer concentrations can also be used.

The electric circuit 2 is activable by applying an electric field and/or a magnetic field M over the same to generate a measurable signal, which is dependent on the total resistance of the circuit 2. Said signal is preferably a measurable current, which is generated in the circuit 2.

Owing to its design the inventive sensor can be mass produced as a disposable sensor at a low cost. The sensor is preferably arranged on a label to be applied to or in the product or product container. The label comprises, for instance, a carrier, to the underside of which an adhesive layer is applied. The sensor forms a layer, which is arranged on the upper side of the carrier. This allows the sensor to be applied in the desired location in a simple way.

When reading the sensor, a magnetic field M is applied, as already mentioned, over the electric circuit 2, and the magnetic field M will be more or less affected as a function of the value of the conductivity of the substrate reaction products.

Advantageously, the sensor can be used to detect moisture in a diaper, for example an incontinence diaper. The sensor is applied to a label in the diaper during manufacturing thereof. To check the diaper during use the signal from the sensor is read by means of a detector in the form of a mobile handheld tool that is applied in the vicinity of the diaper. A detector can also be mounted in the patient's bed forwarding any signals to a control station.

Another field of use for the sensor is detecting the moisture exposure of a moisture-absorbing bulk material. One example thereof may be a fibre-based packaging material. The sensor registers the moisture exposure and when the packaging material is supplied to a packaging machine a device reads the sensor to establish the moisture exposure. The settings of the packaging machine will then be dependent on, inter alia, this moisture exposure.

The sensor may also be used to measure the moisture to which goods, such as packaging material and products, are exposed during transport and during storage. The label comprising the sensor is applied to the goods when the products are packaged and is then checked by means of a detector when the goods have reached their final destination.

The sensor may further be used to check the status in a drying process and to detect liquids in hidden spaces such as leakage from pipes.

It will be understood that the present invention is not limited to the embodiments shown. Several modifications and variations are possible within the scope of the invention. The scope of the invention is thus defined only by the appended claims.

The invention claimed is:

1. A diaper comprising:
   sensor for indicating moisture, the sensor including
      a unit the conductivity of which is moisture exposure dependent and
      an electric circuit,
   said unit being included as a component in said electric circuit, and
   said electric circuit being activable by applying an electric field and/or a magnetic field (M) over the same to generate a measurable signal, which is dependent on the total resistance of the electric circuit, wherein
   said unit comprises an inactive enzyme and a substrate immobilized together on an absorbent material,
      the absorbent material is arranged with a layer of barrier material which allows moisture transport in one direction,
      the inactive enzyme is activated by moisture exposure to catalyse a reaction with the substrate that is dependent on the degree of moisture exposure, the substrate reaction product increasing the conductivity of the unit.

2. A diaper according to claim 1, wherein the reaction product increases the conductivity of the unit as a function of the time and temperature at which moisture exposure occurs.

3. A diaper according to claim 1, wherein the inactive enzyme is selected from one of the following enzyme classes:
Transferases, Hydrolases and Lyases.

4. A diaper according to claim 1, wherein the inactive enzyme is Urease.

5. A diaper according to claim 1, wherein the substrate comprises Urea.

6. A diaper according to claim 1, wherein the absorbent material is filter paper.

7. A diaper according to claim 1, wherein the layer prevents evaporation from the absorbent material.

8. A diaper according to claim 1, wherein the electric circuit, except said unit, is insulated against moisture.

9. A diaper according to claim 1, wherein said signal is a measurable current, which is generated in the electric circuit.

10. A diaper according to claim 1, wherein the electric circuit is an oscillation circuit.

11. A method of indicating moisture in a diaper by means of a sensor, in which
the sensor is arranged on or in the diaper,
an inactive enzyme and a substrate are immobilized together on an absorbent material, the absorbent material is arranged with a layer of barrier material which allows moisture transport in one direction,
the inactive enzyme in the sensor is activated by moisture,
the degradation of the substrate is catalysed by the inactive enzyme,
an electric field and/or a magnetic field is applied over an electric circuit included in the sensor,
a signal generated by the electric circuit is measured, and
the current moisture of the diaper is indicated on the basis of said signal.

12. A diaper according to claim 2, wherein the enzyme is selected from one of the following enzyme classes: Transferases, Hydrolases and Lyases.

13. A diaper according to claim 2, wherein the enzyme is Urease.

14. A diaper according to claim 3, wherein the enzyme is Urease.

15. A diaper according to claim 12, wherein the enzyme is Urease.

16. A diaper according to claim 2, wherein the substrate comprises Urea.

* * * * *